(12) United States Patent
Schmitt et al.

(10) Patent No.: US 8,676,299 B2
(45) Date of Patent: Mar. 18, 2014

(54) METHOD OF DETERMINING PRESSURE IN A VESSEL AS MEASURED BY AN OPTICAL PRESSURE TRANSDUCER IN AN OPTICAL COHERENCE TOMOGRAPHY SYSTEM

(75) Inventors: Joseph M. Schmitt, Andover, MA (US); Christopher Petroff, Groton, MA (US)

(73) Assignee: Lightlab Imaging, Inc., Westford, MA (US)

( * ) Notice: Subject to any disclaimer, the term of this patent is extended or adjusted under 35 U.S.C. 154(b) by 0 days.

(21) Appl. No.: 13/484,936

(22) Filed: May 31, 2012

(65) Prior Publication Data

US 2012/0238869 A1 Sep. 20, 2012

Related U.S. Application Data

(62) Division of application No. 12/689,724, filed on Jan. 19, 2010, now Pat. No. 8,478,384.

(51) Int. Cl.
*A61B 5/00* (2006.01)

(52) U.S. Cl.
USPC ........... 600/427; 600/476; 600/480; 600/486; 600/488; 356/477

(58) Field of Classification Search
USPC ......... 600/407, 425, 476–480, 485, 486, 488; 356/450, 477, 479, 497; 385/115, 116
See application file for complete search history.

(56) References Cited

U.S. PATENT DOCUMENTS

| | | | |
|---|---|---|---|
| 5,085,223 A | 2/1992 | Lars | |
| 5,195,375 A | 3/1993 | Tenerz et al. | |
| 5,321,501 A | 6/1994 | Swanson et al. | |
| 5,349,439 A | 9/1994 | Graindorge et al. | |
| 5,459,570 A | 10/1995 | Swanson et al. | |
| 5,465,147 A | 11/1995 | Swanson | |

(Continued)

FOREIGN PATENT DOCUMENTS

| | | |
|---|---|---|
| JP | 2005-291945 | 10/2005 |
| JP | 2008-142443 | 6/2008 |

(Continued)

OTHER PUBLICATIONS

International Search Report of the International Searching Authority for International Application No. PCT/US2010/062330, mailed Nov. 23, 2011 (6 pgs.).

(Continued)

*Primary Examiner* — Ruth S Smith
(74) *Attorney, Agent, or Firm* — K&L Gates LLP

(57) ABSTRACT

An OCT system and method with integrated pressure measurement. In one embodiment, the system includes an interferometer; a wavelength swept laser; a source arm in communication with the wavelength swept laser; a reference arm in communication with a reference reflector; a first photoreceiver having a signal output; a detector arm in communication with the first photoreceiver, a probe interface; a sample arm in communication with a first optical connector of the probe interface; an acquisition and display system comprising: an A/D converter having a signal input in communication with the first photoreceiver signal output and a signal output; a processor system in communication with the A/D converter signal output; and a display in communication with the processor system; and a probe comprising a pressure sensor and configured for connection to the first optical connector of the probe interface, wherein the pressure transducer comprises an optical pressure transducer.

17 Claims, 13 Drawing Sheets

(56) References Cited

U.S. PATENT DOCUMENTS

| | | |
|---|---|---|
| 5,715,827 A | 2/1998 | Corl et al. |
| 5,748,598 A | 5/1998 | Swanson et al. |
| 5,784,352 A | 7/1998 | Swanson et al. |
| 5,956,355 A | 9/1999 | Swanson et al. |
| 5,984,853 A | 11/1999 | Smith |
| 6,111,645 A | 8/2000 | Tearney et al. |
| 6,112,598 A | 9/2000 | Tenerz et al. |
| 6,134,003 A | 10/2000 | Tearney et al. |
| 6,142,958 A | 11/2000 | Hammarstrom |
| 6,160,826 A | 12/2000 | Swanson et al. |
| 6,167,763 B1 | 1/2001 | Tenerz et al. |
| 6,182,513 B1 | 2/2001 | Stemme |
| 6,191,862 B1 | 2/2001 | Swanson et al. |
| 6,241,651 B1 | 6/2001 | Smith |
| 6,282,011 B1 | 8/2001 | Tearney et al. |
| 6,312,380 B1 | 11/2001 | Hoek |
| 6,343,514 B1 | 2/2002 | Smith |
| 6,421,164 B2 | 7/2002 | Tearney et al. |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,517,481 B2 | 2/2003 | Hoek et al. |
| 6,546,804 B2 | 4/2003 | Stemme |
| 6,552,796 B2 | 4/2003 | Magnin et al. |
| 6,564,087 B1 | 5/2003 | Pitris et al. |
| 6,570,659 B2 | 5/2003 | Schmitt |
| 6,615,667 B2 | 9/2003 | Smith |
| 6,682,489 B2 | 1/2004 | Tenerz et al. |
| 6,692,446 B2 | 2/2004 | Hoek |
| 6,842,254 B2 | 1/2005 | Van Neste et al. |
| 6,868,736 B2 | 3/2005 | Sawatari et al. |
| 6,879,851 B2 | 4/2005 | McNamara et al. |
| 6,891,984 B2 | 5/2005 | Petersen et al. |
| 7,011,636 B2 | 3/2006 | Tenerz |
| 7,044,916 B2 | 5/2006 | Tenerz |
| 7,073,509 B2 | 7/2006 | Tenerz |
| 7,187,453 B2 | 3/2007 | Belleville |
| 7,208,333 B2 | 4/2007 | Flanders et al. |
| 7,241,286 B2 | 7/2007 | Atlas |
| 7,259,862 B2 | 8/2007 | Duplain |
| 7,265,847 B2 | 9/2007 | Duplain et al. |
| 7,285,097 B2 | 10/2007 | Tenerz |
| 7,474,821 B2 | 1/2009 | Donlagic et al. |
| 7,684,657 B2 * | 3/2010 | Donlagic et al. ............... 385/12 |
| 7,689,071 B2 | 3/2010 | Belleville et al. |
| 7,724,148 B2 | 5/2010 | Samuelsson et al. |
| 7,759,633 B2 | 7/2010 | Duplain et al. |
| 7,897,406 B2 | 3/2011 | Pinet et al. |
| 7,946,997 B2 | 5/2011 | Hubinette |
| 8,174,395 B2 | 5/2012 | Samuelsson |
| 8,216,151 B2 | 7/2012 | Smith |
| 2002/0095179 A1 | 7/2002 | Tenerz et al. |
| 2003/0220588 A1 | 11/2003 | Tenerz et al. |
| 2004/0215166 A1 | 10/2004 | Atlas |
| 2005/0201662 A1 | 9/2005 | Petersen et al. |
| 2006/0009817 A1 | 1/2006 | Tulkki |
| 2006/0095065 A1 | 5/2006 | Tanimura et al. |
| 2006/0161224 A1 | 7/2006 | Samuelsson et al. |
| 2006/0233484 A1 | 10/2006 | Van Neste et al. |
| 2006/0241503 A1 | 10/2006 | Schmitt et al. |
| 2007/0177152 A1 | 8/2007 | Tearney et al. |
| 2007/0179487 A1 | 8/2007 | Tearney et al. |
| 2007/0260198 A1 | 11/2007 | Atlas |
| 2007/0274650 A1 | 11/2007 | Tearney et al. |
| 2007/0282403 A1 | 12/2007 | Tearney et al. |
| 2008/0140325 A1 | 6/2008 | Teramura |
| 2008/0159687 A1 | 7/2008 | Donlagic et al. |
| 2008/0161696 A1 | 7/2008 | Schmitt et al. |
| 2008/0165366 A1 | 7/2008 | Schmitt et al. |
| 2008/0197750 A1 | 8/2008 | Katardjiev et al. |
| 2009/0082678 A1 | 3/2009 | Smith |
| 2009/0204009 A1 | 8/2009 | Powers et al. |
| 2010/0234698 A1 * | 9/2010 | Manstrom et al. ............ 600/301 |
| 2010/0241008 A1 | 9/2010 | Belleville et al. |
| 2011/0066047 A1 | 3/2011 | Belleville et al. |
| 2011/0137140 A1 | 6/2011 | Tearney et al. |
| 2012/0108956 A1 | 5/2012 | Warger et al. |
| 2012/0136244 A1 | 5/2012 | Manstrom et al. |
| 2012/0310081 A1 * | 12/2012 | Adler et al. ................... 600/427 |

FOREIGN PATENT DOCUMENTS

| | | |
|---|---|---|
| WO | 2006032128 | 3/2006 |
| WO | 2006058423 | 6/2006 |
| WO | 2006066393 | 6/2006 |
| WO | 2010105356 | 9/2010 |
| WO | 2011088572 | 7/2011 |
| WO | 2012061935 | 5/2012 |

OTHER PUBLICATIONS

Jung et al., "A diabatically tapered splice for selective excitation of the fundamental mode in a multimode fiber," Optics Letters, 34:15, Aug. 1, 2009 (2369-2371).

Pijls et al., "Measurement of Fractional Flow Reserve to Assess the Functional Severity of Coronary-Artery Stenoses," The New England Journal of Medicine, 334:26, Jun. 27, 1996 (1703-1708).

* cited by examiner

METHOD OF DETERMINING PRESSURE IN A VESSEL AS MEASURED BY AN OPTICAL PRESSURE TRANSDUCER IN AN OPTICAL COHERENCE TOMOGRAPHY SYSTEM

CROSS REFERENCE TO RELATED APPLICATIONS

This application is a divisional of U.S. application Ser. No. 12/689,724, filed on Jan. 19, 2010, the entire disclosure of which is incorporated by reference herein.

FIELD OF INVENTION

This invention relates generally to invasive medical devices and more specifically to fiber-optic systems for imaging the lumen of blood vessels and for measuring physiological variables such as blood pressure.

BACKGROUND

The functional severity of a stenotic lesion in an artery can be assessed by measuring the pressure gradient across the lesion. Intravascular pressure measurement, particularly in the coronary arteries, has gained widespread acceptance as a tool for guiding catheter-based interventional procedures. Angioplasty or stenting of lesions in coronary arteries can be avoided if the fractional flow reserve (FFR), defined as the ratio of the blood pressures measured distal to and proximal to a lesion after injection of a vasodilating drug, exceeds a certain clinically defined threshold.

Various devices have been developed for sensing arterial pressure at the tip of miniature catheters during medical diagnostic and interventional procedures. The most widely used device of this type, often referred to as a "pressure wire," employs an electronic pressure transducer embedded in the side of a long metallic tube through which electrically conducting wires pass to a connector at the proximal end. Typically, the transducer is mounted at a distance 1-2 cm proximal to a spring at the distal tip of the tube. The operator navigates the tube through the artery manually until the transducer reaches the desired location for local pressure measurement.

One drawback of electronic pressure measurement systems is the relatively large minimum diameter of the pressure wire, which is determined by the size of the transducer, wires, and wire attachment assembly. The diameter of a pressure wire is critically important, because it must pass through narrow stenoses in blood vessels without significantly increasing the pressure gradient across the stenosis or preventing passage of the wire through the stenosis. This is especially significant because diseased arteries that are candidates for angioplasty, for example, can have lumen diameters smaller than 1 mm.

A second drawback of electronic pressure monitoring systems is their susceptibility to electrical interference and calibration drift. Careful sealing of the wires and transducer to avoid moisture intrusion and shielding of the wires against electromagnetic interference are required to minimize environmental disturbances.

Frequently, acquisition of intravascular images and measurement of intravascular pressures during a single medical procedure is desirable. However in such an application, when intended to be used with imaging catheters, electronic pressure wires, because of their wire connections, are difficult to integrate with intravascular imaging catheters.

The present invention addresses these issues.

SUMMARY OF THE INVENTION

The present invention relates to a method and apparatus for providing cost-effective pressure monitoring capabilities to an intravascular optical coherence tomography (OCT) system. The combined system permits convenient use of both modalities from a single system console in which processing, catheter control, and parameter and image display are controlled by software executing on the same computer.

The invention provides, in part, an OCT system with integrated pressure measurement. The OCT system in one embodiment includes: an interferometer, an acquisition and display system, and a probe including a pressure sensor. The interferometer in one embodiment includes: a wavelength swept laser; a source arm in optical communication with the wavelength swept laser; a reference arm in optical communication with a reference reflector; a first photodetector having a signal output; a detector arm in optical communication with the first photodetector; a probe interface; and a sample arm in optical communication with a first optical connector of the probe interface. The acquisition and display system in one embodiment includes: an analog to digital converter having a signal input in electrical communication with the first photodetector signal output and a signal output; a processor system in electrical communication with the analog to digital converter signal output; and a display in electrical communication with the processor system. The probe in one embodiment is configured for optical connection to the first optical connector of the probe interface, and the pressure transducer includes an optical pressure transducer.

In some embodiments of the OCT system, the analog to digital converter further includes a sample clock input and a trigger input, and the OCT system further includes: a power splitter having a first arm in optical communication with the wavelength swept laser, a second arm in optical communication with the source arm of the interferometer, and having a third and forth arm; a trigger generator in optical communication with the third arm of the power splitter, and having a trigger output; and a sample clock generator in optical communication with the forth arm of the power splitter and having a sample clock output. The trigger output of the trigger generator and the sample clock output of the sample clock generator is in electrical communication with the trigger input and sample clock input of the analog to digital computer, and the analog to digital converter can convert a signal from the first photo detector in response to a trigger signal from the trigger generator and a sample clock signal from the sample clock generator.

In some embodiments, the OCT system further includes an optical switch in optical communication between the reference arm and the reference reflector.

In some embodiments, the probe of the OCT system further includes an OCT imaging optical system.

In some embodiments, the OCT system includes: a second light source; a spectrometer having an optical input and an electrical signal output; an optical circulator having a first arm in communication with the second light source, a second arm in optical communication with the spectrometer optical input, and a third arm; and a wavelength division multiplexer in optical communication between the sample arm of the interferometer and the probe interface and having a third arm in optical communication with the third arm of the optical circulator, where the electrical signal output of the spectrometer is in electrical communication with the processor system.

In some embodiments of the OCT system, the analog to digital converter has a second signal input; the power splitter further includes a fourth arm; the probe interface further includes a second optical connector; and the OCT system further includes: a second photodetector, the second photodetector including an electrical signal output and a optical signal input and a circulator. The circulator includes: a first arm in optical communication with the fourth arm of the power splitter; a second arm in optical communication with the optical input of the second photodetector; and a third arm in optical communication with the second optical connector of the probe interface, and the electrical signal output of the second photodetector can be in electrical communication with the second signal input of the analog to digital converter.

In some embodiments of the OCT system, the circulator is a multimode circulator and the third arm of the circulator is a multimode fiber; and the optical coherent tomography system further includes a single mode to multimode converter optically connected between the power splitter and the multimode circulator. The fourth arm of power splitter includes a single mode optical fiber, and the first arm of the circulator includes a multimode optical fiber.

The invention also provides, in part, a probe for an OCT system. The probe in one embodiment includes: a body defining a bore and having a first end and a second end; an optical fiber located within the bore, the optical fiber having a first end and a second end; an optical pressure transducer located within the bore and in optical communication with the first end of the optical fiber; and a fiber optic connector, located at the second end of the body and in optical communication with the second end of the optical fiber, where the body further defines at least one opening from the bore to the environment by which pressure from the environment is transmitted to the optical pressure transducer. In some embodiments, the second end of the optical fiber includes a fiber optic ferrule.

In some embodiments, the probe further includes a spring tip positioned at the first end of the body.

In some embodiments, the probe further includes a removable torque handle removably attached to the body.

In some embodiments of the probe, the fiber optic connector defines a bore and includes a mating unit sized and configured to receive the fiber optic ferrule, and the fiber optic connector further includes a locking clamp to removably attach the body to the fiber optic connector.

In some embodiments of the probe, the body further includes a guide having a first end and a second end, the guide positioned at the first end of the body and defining a second bore, the second bore sized and shaped to permit a guide wire to enter the guide through a first opening in the first end of the guide and to pass through the second bore and out through a second opening in the guide. In some embodiments, the optical fiber and the optical pressure transducer are movable within the bore. In some embodiments, the optical fiber passes through a liquid seal located in the bore adjacent the fiber optic connector.

The invention also provides, in part, a combination probe for an OCT system. The combination probe includes: a body having a wall defining a bore and having a first end and a second end; an optical fiber located within the bore, the optical fiber having a first end and a second end; a partial reflector located within the bore and positioned to reflect a first portion of light received from the first end of the optical fiber from through the wall of the body; an optical pressure transducer located within the bore and positioned to receive a second portion of light from the first end of the optical fiber; and a fiber optic connector, located at the second end of the body and in optical communication with the second end of the optical fiber, where the body further defines at least one opening from the bore to the environment by which pressure from the environment is transmitted to the optical pressure transducer.

The invention also provides, in part, a method of determining pressure in a vessel as measured by an optical pressure transducer in an OCT system which includes an interferometer having a photodetector located in a detector arm of the interferometer and having an optical pressure transducer located in the sample arm of the interferometer. The method includes the steps of sampling a signal from the photodetector to form a sampled pressure signal; normalizing the sampled signal to obtain a normalized sampled pressure signal; removing cavity noise to form a cleaned normalized sampled pressure signal; finding a minimum value in the cleaned normalized sampled pressure signal; and tracking the minimum value of the cleaned normalized sampled pressure signal. In some embodiments of the method, the minimum value is determined by one of convolution, differentiation and gradient searching. In some embodiments, the method further includes the steps of: inserting a catheter having an optical pressure transducer into a vessel; and moving the optical pressure transducer within the catheter.

The invention also provides, in part, a method of obtaining an OCT image in a blood vessel using an OCT/pressure probe system. The method includes the steps of inserting a combination OCT/pressure probe catheter into the blood vessel; setting the OCT/pressure probe system to measure pressure; determining the pressure drop across a putative stenotic region of the vessel; setting the OCT/pressure probe system to image; and taking an OCT image of the putative stenotic region.

This Summary is provided merely to introduce certain concepts and not to identify any key or essential features of the claimed subject matter.

BRIEF DESCRIPTION OF THE DRAWINGS

The objects and features of the invention can be understood more completely by referring to the drawings described below and the accompanying descriptions.

FIG. 6b is a cross-sectional view of the proximal end of a steerable intravascular pressure probe of FIG. 6a.

FIG. 7b is a cross-sectional view of the proximal end of a steerable intravascular pressure wire with a detachable optical adapter of FIG. 7a.

FIG. 8b is a cross-sectional view of the proximal end of a rapid-exchange intravascular catheter with a single pressure sensing port of FIG. 8a.

FIG. 9b is a cross-sectional view of the proximal end of a rapid-exchange intravascular catheter with multiple pressure sensing ports of FIG. 9a.

DETAILED DESCRIPTION

The following description refers to the accompanying drawings that illustrate certain embodiments of the invention. Other embodiments are possible and modifications can be made to the embodiments without departing from the spirit and scope of the invention. Therefore, the following detailed description is not meant to limit the present invention. Rather, the scope of the present invention is defined by the claims.

Figure 1:
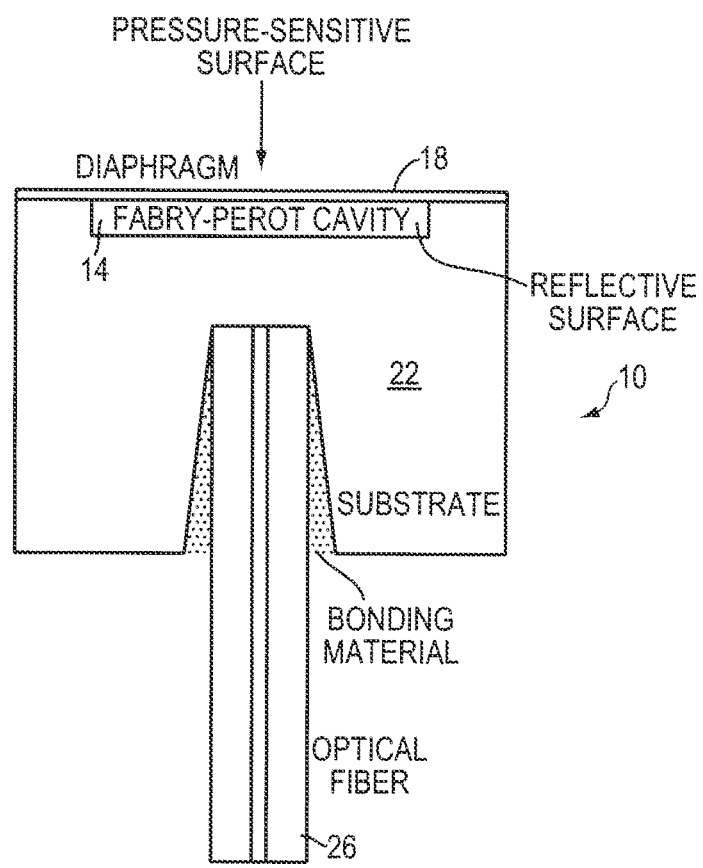
FIG. 1 illustrates an embodiment of the design of an optical pressure transducer known to the prior art that is suitable for use with the Fourier-domain optical coherence tomography system.

The present invention arises from the realization that the basic architecture of a frequency-domain OCT (FD-OCT) system, configured in a specific manner, permits a user to make an intravascular blood pressure measurement when used in conjunction with fiber-optic Fabry-Perot pressure transducers. FIG. 1 illustrates the basic structure of a Fabry-Perot optical pressure transducer 10, known to the prior art, that is compatible with the combined OCT imaging/pressure measurement system disclosed herein. A Fabry-Perot cavity 14 is formed by the surfaces of a diaphragm 18 and the sensor body 22 and has a reflectivity that depends on optical frequency or wavelength of the light exiting the optical fiber 26.

The depth of the cavity lies typically within the range of 1-20 μm and its width, which is limited by the diameter of the body of the sensor, lies typically in the range of 0.15-0.4 mm. Light from an optical fiber 26 impinges on the cavity 14 and the same fiber 26 collects the reflected light as the diaphragm 18 flexes in response to external pressure variations. When the sensor 10 is excited by a laser, the optical signals returning from the cavity 14 through the optical fiber 26 combine and generate a common-mode interference signal. An PD-OCT system, configured according to the present invention, performs the functions required to record these interference signals. Algorithms are discussed below for processing the interference signals and displaying blood pressure waveforms.

Figure 2:
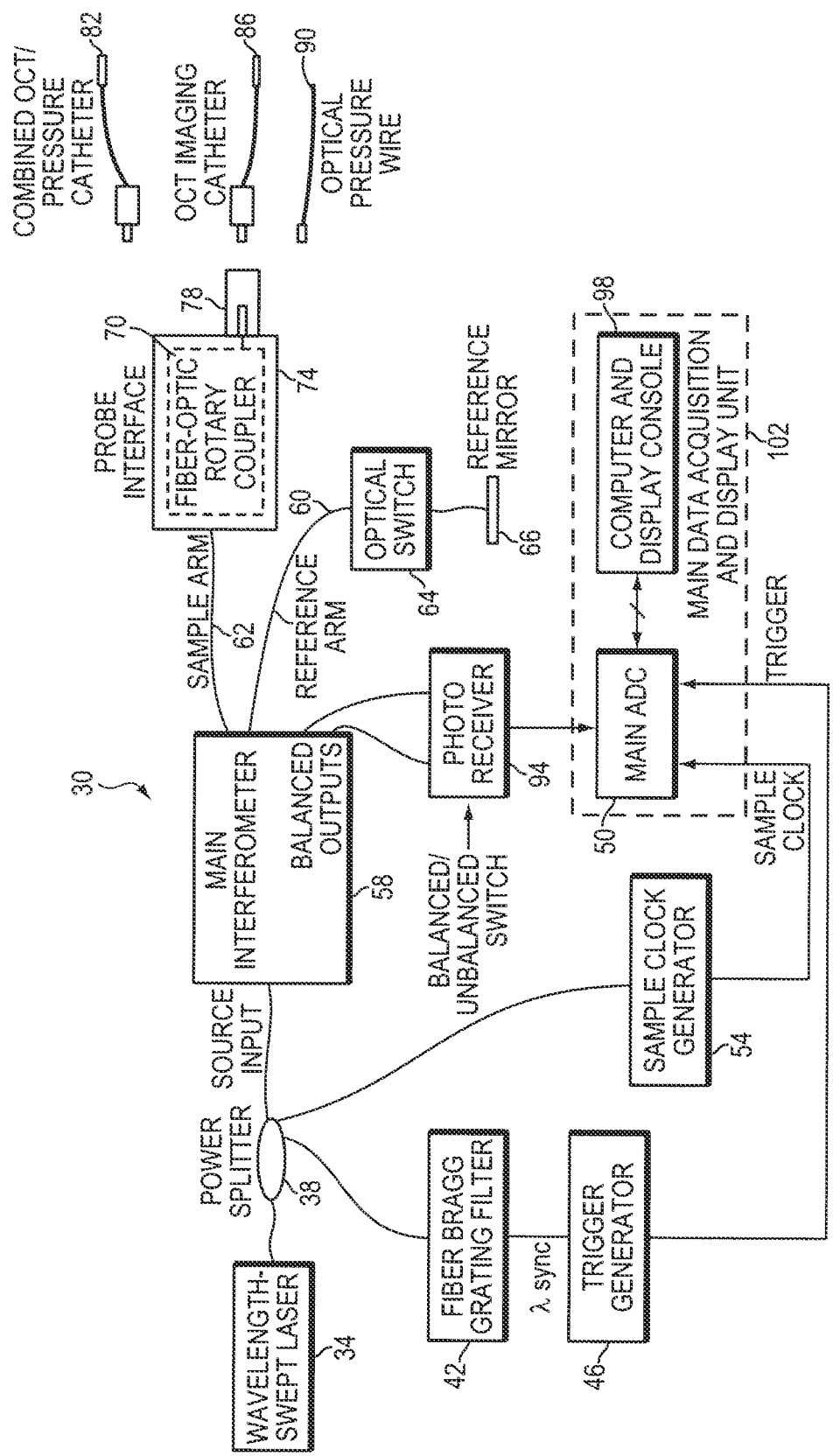
FIG. 2 is a block diagram of an embodiment of an FD-OCT imaging system that is capable of collecting data from an optical pressure sensor or OCT imaging probe according to the present invention.

One embodiment of an FD-OCT system 30 that is suitable for combined OCT imaging and blood pressure measurement according to the present invention is shown in FIG. 2. Because it performs both functions with little additional hardware, it is a simple cost-effective embodiment of the combined system. A wavelength-swept laser 34 (also referred to as an 'optical-frequency tunable laser' or 'swept-source laser') emits nearly monochromatic (line width<0.2 nm) near-infrared light within a specific spectral band suitable for intravascular OCT imaging. The most common band of emission wavelengths lies within the telecommunications O band (1260≤λ≤1360 nm). The wavelength of the laser 34 is swept or stepped rapidly over a broad band of wavelengths. The sweep is completed typically within a period less than 20 μs and repeats 10,000 times or more each second. An optical power splitter 38 separates the light into three channels. The first channel, which includes a fiber Bragg grating filter 42 (or equivalent wavelength-selective filter) with a narrow bandpass (typically <1 nm) and a trigger generator 46, provides a timing pulse to the main analog-to-digital converter 50 that triggers the data acquisition. This channel produces a tinting pulse at a predetermined optical frequency or wavelength (typically 238 THz or 1260 nm) when the output of the laser sweeps through the passband of the fiber Bragg grating filter. The timing pulse triggers the start of the acquisition of the analog signals from the photoreceiver on each edge of the sample clock.

Light in the second channel is routed through a single-mode optical fiber to a sample clock generator 54, which includes a reference interferometer and associated electro-optics that generate sample clock pulses at fixed optical frequency intervals. The sample clock generator ensures that the signals from photoreceiver 94 are collected by the data acquisition and display unit 102 synchronously with the sweep of the laser 34 at known wavelength steps. A fiber-optic Mach-Zehnder, Michelson interferometer, optical etalon, or equivalent type of interferometer with a known optical path difference can serve as the reference interferometer of the clock generator 54.

Light in the third channel is conducted through a single-mode optical fiber to the main interferometer 58 which splits the light into reference 60 and sample arms 62. The light in the reference arm passes through an optical switch 64 to a reference mirror 66 that sets the zero-point optical delay for the imaging system and determines the depth into the tissue at which the OCT imaging will take place. The light in the sample arm 62 passes to a motorized fiber-optic rotary coupler 70 in the probe interface 74. The probe interface 74 includes a connector 78 which permits various probes (combined OCT imaging/pressure measuring catheter 82, OCT imagining 86 or optical pressure measuring probe 90) to connect to the sample arm 62 of the interferometer 58.

A motorized translation stage in the probe interface 74 enables the fiber-optic core of the catheter (82, 28, 90) inserted into a vessel to pull back with a constant speed. The optical output of the main interferometer 58 is converted by the photoreceiver 94 to electrical signals representative of the interference signals from the sample 60 and reference arms 62 of the interferometer 58. These electrical signals are converted to digital signals by the analog to digital converter (A/D) 50 and processed and displayed on the display unit 98 of the data acquisition system 102. Because the trigger generator 46 and clock generator 54 are synchronized, the absolute optical frequency of the interference signal acquired by the data acquisition system 102 during every laser sweep can be determined from the number of sample clock pulses acquired after each trigger pulse from the trigger generator 46. The absolute frequency reference is provided, by the fiber-Bragg grating, which indicates the starting optical frequency; subsequent steps occur at equal optical frequency intervals set by the sample clock generator.

In one embodiment of the invention shown in FIG. 2 operates either in the OCT imaging mode, pressure mode, or combined OCT/pressure mode depending on whether an OCT imaging 86 catheter, pressure probe 90, or combined OCT/pressure catheter 82 is attached to the probe interface connector 78. The mode of operation can be selected manually or automatically, depending on the system configuration. Manual selection requires the user to choose the operating mode from a software menu. Automatic selection can be accomplished in one of several ways.

In one embodiment with the motorized fiber-optic rotary coupler 70 in a stationary position, data acquisition unit 102 initiates after either the OCT imaging catheter 86 or pressure probe 90 has been inserted. A software algorithm identifies the type of probe according to the interference signal pattern detected by the main interferometer 58 and photodetector 94 and loads the appropriate control and display software. Once the pressure measurement has been completed, the precise location and the severity of the stenosis can be determined and the OCT imaging procedure can begin.

In a second embodiment of the system to automatically determine what type of probe is connected to the system, following insertion of the catheter 86 or pressure probe 90, the system attempts to rotate the motorized fiber-optic rotary coupler 70. A torque sensor in the motor of the motorized coupler 70 measures resistance to rotation. Torque exceeding a specific threshold indicates that a pressure probe 90, with a non-rotating proximal connection, is attached. Once insertion of a pressure probe 90 has been detected, the motor disengages and the appropriate control and display software loads.

In a third embodiment, an encoded electrical or optical tag (e.g., bar code, wire-encoded electrical connector, RFID tag, flash memory chip) on the proximal end of the OCT imaging catheter 86 or pressure probe 90 (or both 82) is read by the system to identify the appropriate mode of operation. The tag can be read automatically by the probe interface 74 when the probe is inserted or, alternatively, a handheld device can be employed to read the marker from the body or package of the probe. This method of probe identification has the advantage that additional factory calibration data encoded in the markers can be read at the same time.

In addition to features that enable automatic software configuration, the system of FIG. 2 also contains features that enable automatic hardware configuration once the operational mode has been determined. In the standard OCT imaging mode, optical switch 64 is actuated, allowing light to reflect from the reference mirror 66. However, in the pressure-measurement mode, because the system records common-mode interference signals and no reference light is required, the optical switch 64 is turned off, isolating the reference reflector 66 from the reference arm 60 of the interferometer 58. In addition, since differential (balanced) photodetection is employed, only during OCT imaging, the electronic balancing circuits in the photoreceiver 94 are switched to the single-ended (unbalanced) mode during pressure measurements.

Figure 3:
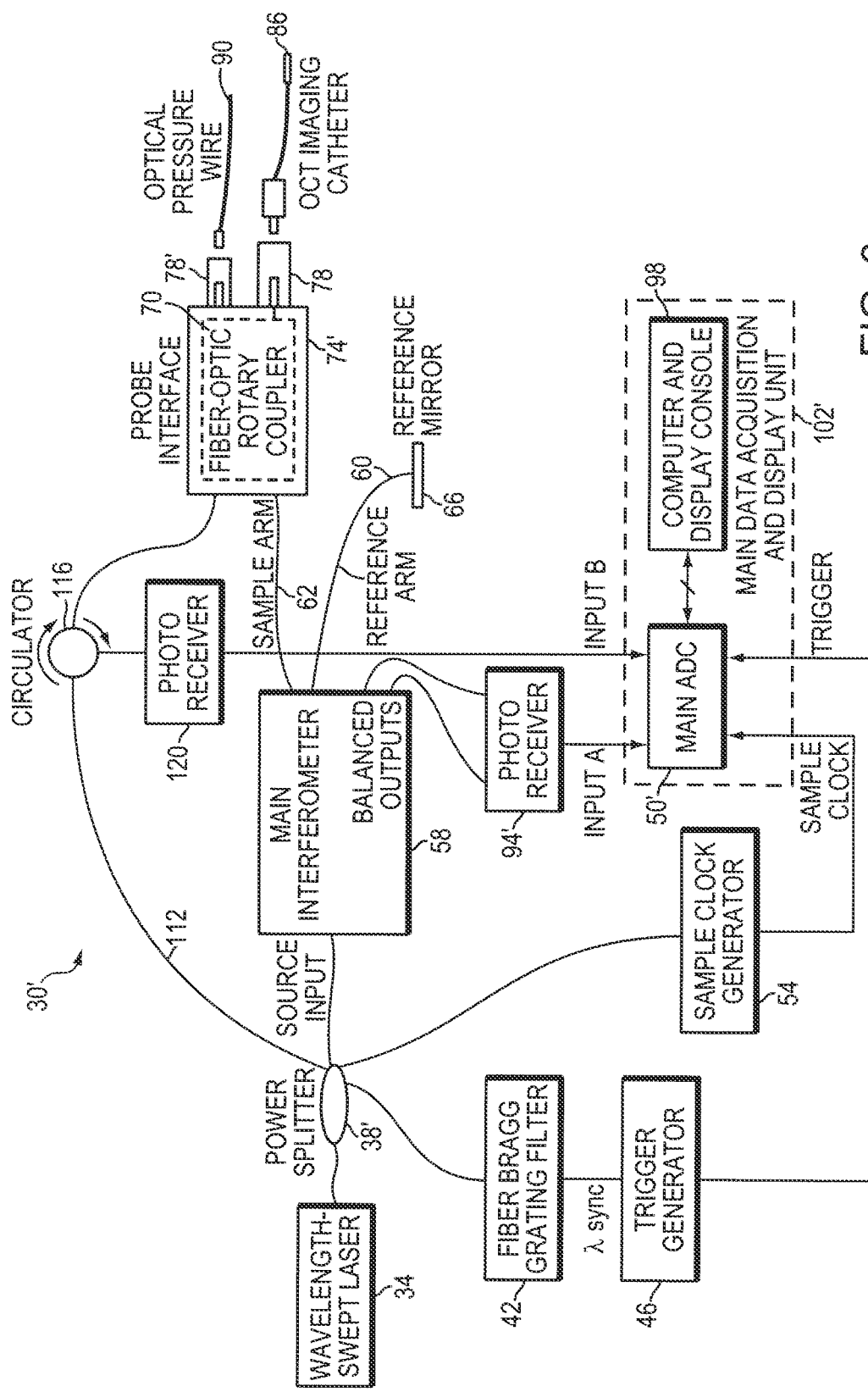
FIG. 3 is a block diagram of another embodiment of an FD-OCT imaging system that is capable of collecting data from an optical pressure sensor or OCT imaging probe according to the present invention.

FIG. 3 is a block diagram of another embodiment 30' of the invention in which separate optical connections are provided on the probe interface 74' for the OCT imaging catheter 86 and optical pressure probe 90. This configuration enables acquisition of blood pressure measurements with a separate pressure probe 90 before, during, or after OCT imaging. Measurement of pressure during OCT imaging can be accomplished by inserting both probes in the blood vessel at the same time. An additional optical channel 112 from the power splitter 38' directs light to the pressure probe 90 through an optical circulator 116. The optical circulator 116 re-directs the light that returns from the pressure probe 90 into a second photodetector 120 that generates the electronic signal corresponding to interference signals from which the pressure measurements are derived. These signals are digitized by a second channel of the analog to digital converter 50' and recorded by the same data acquisition system 102' used to record the OCT interference signals. In contrast to the first embodiment of the invention illustrated by FIG. 2, no optical switch 64 is required in the reference arm 60 to isolate the reference arm 60 from the reference reflector 66 (FIG. 2) during pressure measurement.

Figure 4:
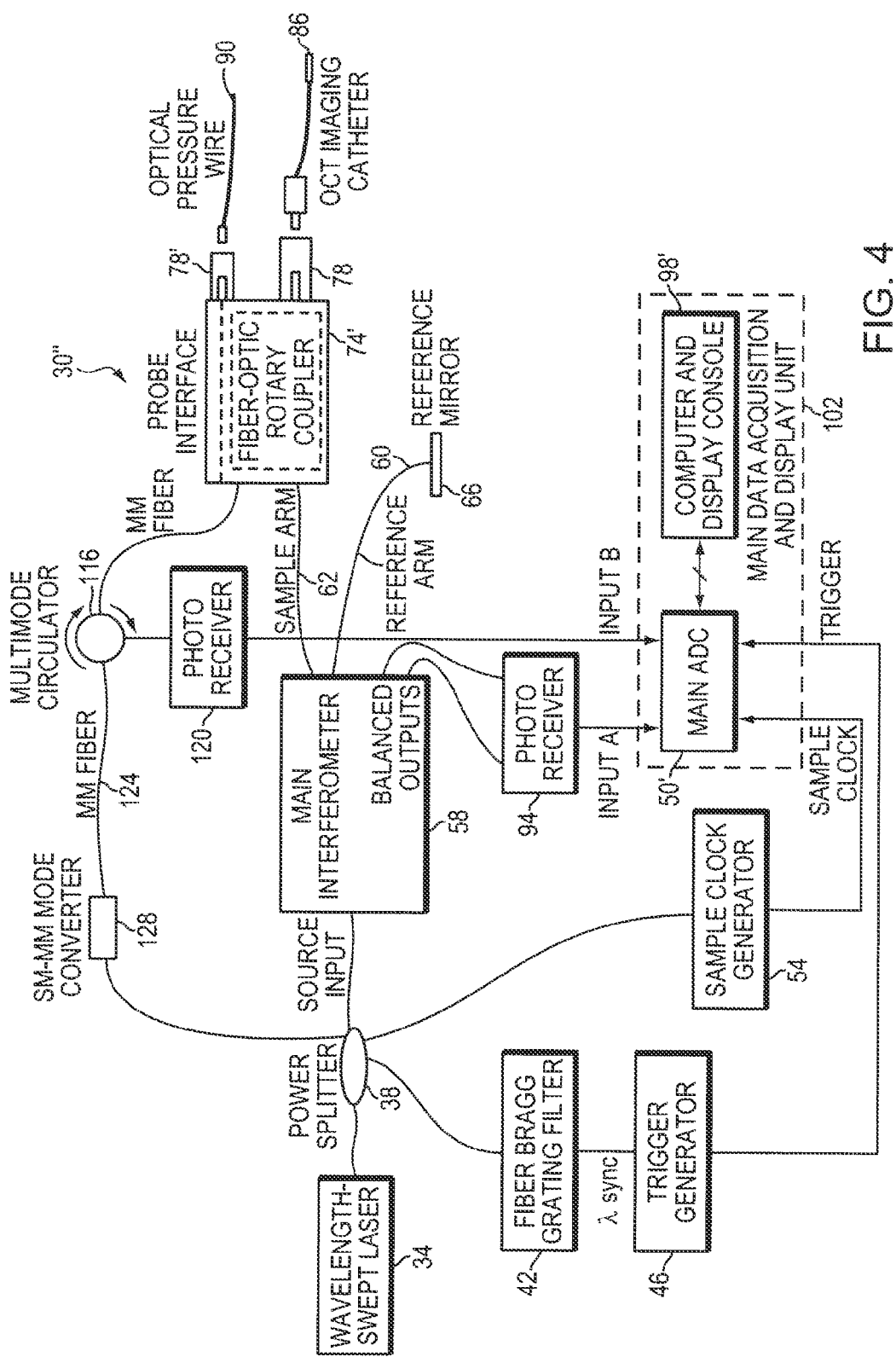
FIG. 4 is a block diagram of yet another embodiment of an FD-OCT imaging system that is capable of collecting data from an optical pressure sensor according to the present invention using a multi-mode optical pressure probe.

A third embodiment of invention 30", illustrated in FIG. 4, is similar to that shown in FIG. 3, except a multi-mode (MM) fiber 124 is used instead of a single-mode (SM) fiber 112 to conduct light over part of the path from the laser 34 to the optical pressure probe 90. The larger core of the multi-mode (MM) fiber 124 facilitates fabrication of the pressure probe and reduces the tolerances for aligning the fiber-optic connection at the probe interface 78' to the proximal end of the pressure probe. Typically, a 50-μm or 62.5-μm diameter graded-index MM telecommunications fiber may be used in this application. To reduce inter-modal interference noise, a passive SM-to-MM converter 128, may be employed to launch light from the laser 34 into the MM fiber 124.

Figure 5:
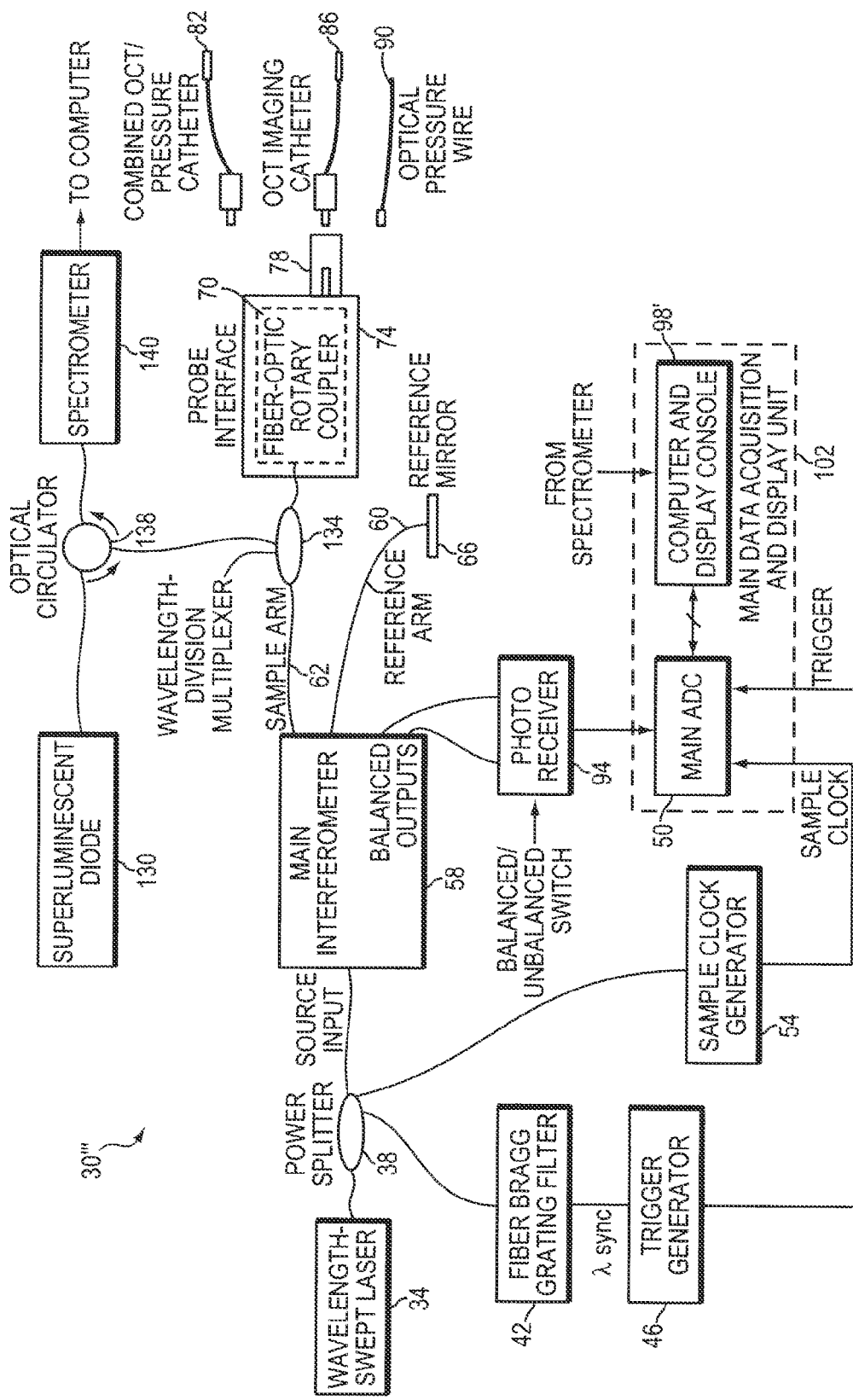
FIG. 5 is a block diagram of still yet another embodiment of an FD-OCT imaging system that is capable of collecting data from an OCT imaging catheter and an optical pressure sensor operating in different optical wavelength bands.

FIG. 5 illustrates a fourth embodiment 30''' of the invention that enables simultaneous acquisition of OCT images and pressure measurements from a single fiber-optic catheter that contains both an OCT optical lens assembly and an optical pressure transducer as described below. The OCT and pressure interference signals are detected in two non-overlapping wavelength bands, for example, 1250-1350 nm and 1500-1600 nm or 1000-1200 nm and 1500-1600 nm, respectively. A superluminescent diode 130 emits broadband light that combines with the OCT laser light in a wavelength-division multiplexer 134 after passing through an optical circulator 138. The combined light from the main interferometer 58 sample arm 62 and the superluminescent diode 130 travels in the same SM optical fiber to the tip of the catheter where light in the appropriate band (as described below in conjunction with the probe) impinges upon and reflects from either the tissue or the pressure transducer The reflected light is passed back down the fiber and separated again into two wavelength bands by the wavelength division multiplexer 134. Light reflected by the tissue in first band enters the main OCT interferometer 58 through the sample arm 62 and light reflected by the pressure transducer in the second band enters a spectrometer 140 again after passing through the optical circulator 138. The spectrometer 140 records the spectrum of the light reflected from the pressure transducer and transmits the spectral data to the processor and display system 98' over a digital interface.

FIGS. 6-10 illustrate the designs of pressure-sensing catheters that are compatible with an FD-OCT system configured according to the various embodiments of the invention. Each of the catheters contains a miniature optical pressure sensor at the tip of a small-diameter (80 μm- or 125 μm-diameter)

optical fiber. The diameters of the sensor and fibers are small enough to enable the fabrication of pressure-sensing catheters with dimensions of coronary and neurovascular guide wires (0.010-0.014").

Figure 6A:
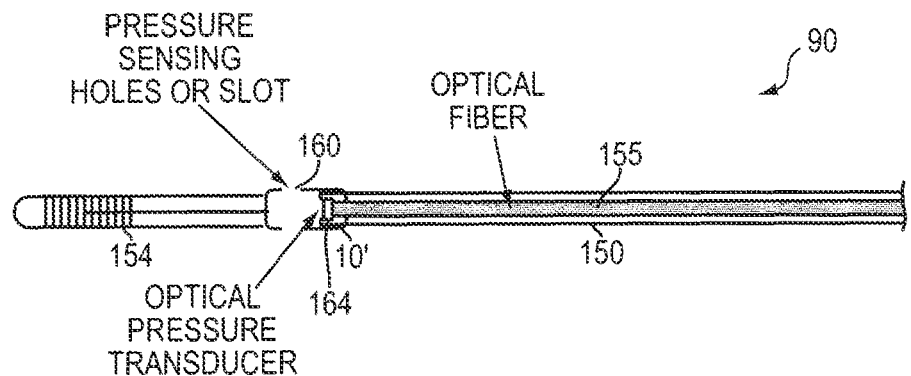
FIG. 6a is a cross-sectional view of the distal end of an embodiment of a steerable intravascular pressure probe constructed in accordance with the invention.
Figure 6B:
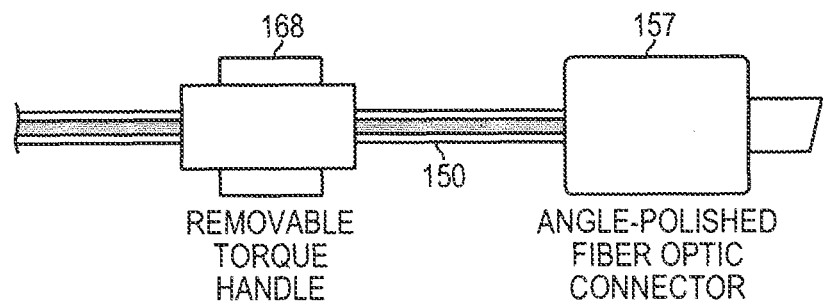

FIGS. 6(a-b) show cross-sectional views of the proximal and distal ends of one of the embodiments of the optical pressure probe. The pressure probe 90 includes of a long hollow flexible tube 150 or an assembly of tapered tubes with an optical transducer 10' mounted at the base of a spring tip 154 located at the distal end of the probe. The optical fiber 155 from the pressure transducer 10' connects to a fiber-optic connector 157 mounted on the proximal end of the probe. Pressure-sensing slots or holes 160 in the mounting collar 164 at the base of the spring tip 154 transmit the blood pressure from the vessel in which the probe is inserted to the diaphragm 18 of the pressure transducer 10'. Alternatively the optical pressure transducer 164 is exposed to the blood flow directly. Preferably, the hollow body of the tube 150 is composed of a metal, metal alloy, or metal-braided polymer that gives the tube sufficient resistance to compression and rigidity to torque, while maintaining a high degree of flexibility.

To minimize the restriction of flow caused by placement of the probe across a tight stenosis in a blood vessel, the body of the probe at its distal end is fabricated typically with an outer diameter of 0.010-0.018" (0.25-0.46 mm). To position the pressure probe, the operator inserts the probe through a guide catheter into the artery and steers the probe to the target location using a torque handle 168 located near the proximal end. In accordance with the design of the FD-OCT system of FIG. 2, operating in the pressure measurement mode, the fiber-optic rotary coupler 70 in the probe interface 74 rotates passively. The tip of the pressure probe 90 can be steered to the target location in the blood vessel by disconnecting the fiber-optic connector from the probe interface to allow free rotation of the body of the probe. After the pressure wire has been positioned, the fiber-optic connector can then be reinserted into probe interface to obtain pressure measurements. Alternatively, since the fiber-optic rotary coupler in the probe interface rotates passively, the tip of the pressure probe can be steered without disconnecting the fiber-optic connection. Fabricating the pressure probe with a longer body (~2 meters) facilitates this alternative steering method. If the probe interface does contain a rotatable element, the proximal end of the transducer may be made flexible between the removable torque handle 168 and the angle polished fiber optic connector 157. This allows the pressure wire to be steered with a simpler probe interface unit.

Figure 6C:
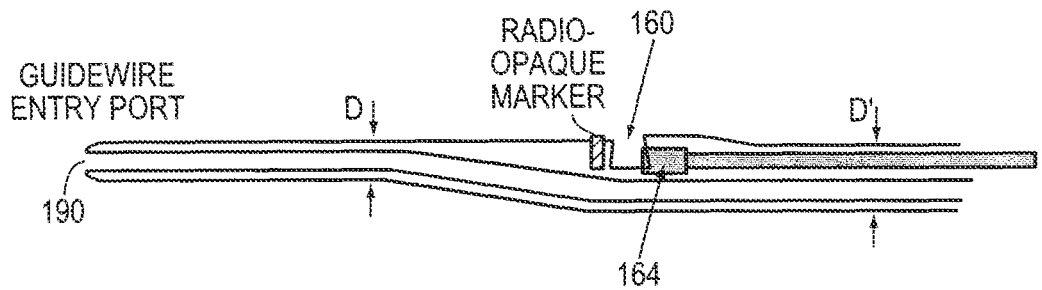
FIG. 6c is a cross-sectional, view of the distal end of an embodiment of the probe in which the tube diameters proximal and distal the transducer are smaller than the tube diameter adjacent the transducer.

It should be noted that the diameter of the probe need not be constant across the transducer. FIG. 6c depicts a cross-sectional view of the probe of FIG. 6a but in which the diameter of the probe varies. The widths distal (D) and proximal (D') to the transducer 164 are less that the width necessary to encompass the transducer 164. This configuration functions because the wider diameter at the transducer 164 and opening 160 is not located within the stenotic region when pressure is measured. Hence, the diameter of the vessel in the region outside the stenosis is sufficiently large to permit pressure to enter through hole 160 without constricting flow and generating an anomalous pressure reading.

Figure 7A:
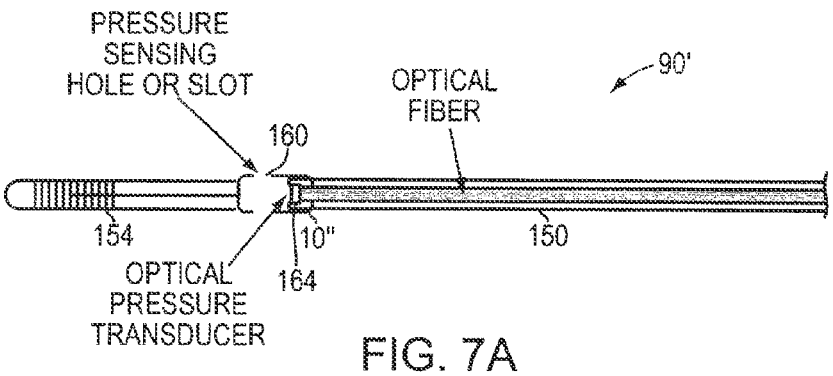
FIG. 7a is a cross-sectional view of the distal end of an embodiment of a steerable intravascular pressure wire with a detachable optical adapter constructed in accordance with the invention.
Figure 7B:
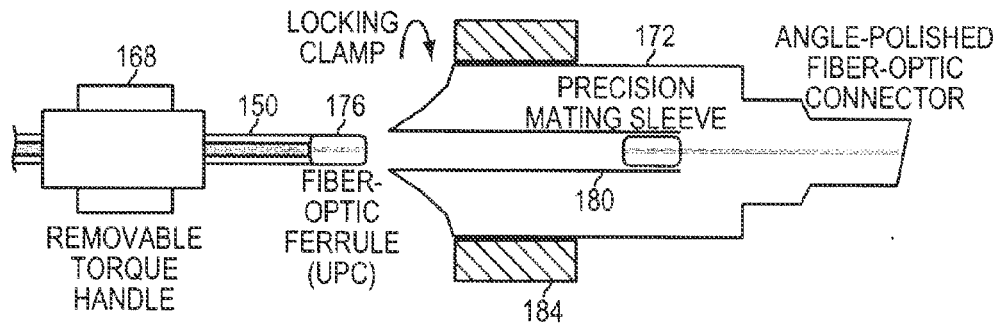

FIGS. 7(a-b) show cross-sectional views of an alternative construction of an optical pressure probe. Similar to the probe shown in FIG. 6, the distal end of the probe shown here is constructed from a long flexible hollow tube 150 or an assembly of tapered tubes with the pressure sensing port located at the base of its spring tip 154. However, the probe shown in FIG. 7b includes a disposable optical adapter 172 that gives the operator access to the proximal end of the adapter. This configuration enables the pressure probe to serve as a primary guide wire over which a balloon catheter or other interventional device can be inserted into the artery. For compatibility with standard devices employed in coronary interventions, the pressure probe is fabricated, with an outer diameter of less than 0.014" (0.36 mm) over its entire length. An end-polished fiber-optic ferrule 176, with an outer diameter approximately equal to that of the body of the probe, mates precisely with a similar fiber-optic sleeve 180 inside the optical adapter 172. To maintain a high optical transmission during free rotation of the proximal end, while minimizing back reflection, the mating fiber-optic ferrules 176, 180 are fabricated, preferably, with Ultra Physical Contact (UPC) polished end faces. In some embodiments, separate disposable optical adapter 172, which is supplied to the user as a separate sterilized component, plugs into the probe interface of the FD-OCT system and remains connected throughout the procedure. At the completion of the procedure, the adapter and the probe are removed as a unit by the user for disposal.

To position the pressure probe 90', the operator the proximal end of the probe 90' from the optical adapter 172, inserts the probe 90' through a guide catheter into the artery, and steers the probe 90' to the target location using the removable torque handle 168 at the distal end. Once the wire has been positioned and any additional device has been inserted over the pressure probe, the operator re-inserts the proximal end of the probe into the optical adapter 172 and locks the clamp 184 to keep the surfaces of the optical fibers 176, 180 in close contact if the pressure probe 90' moves.

Figure 8A:
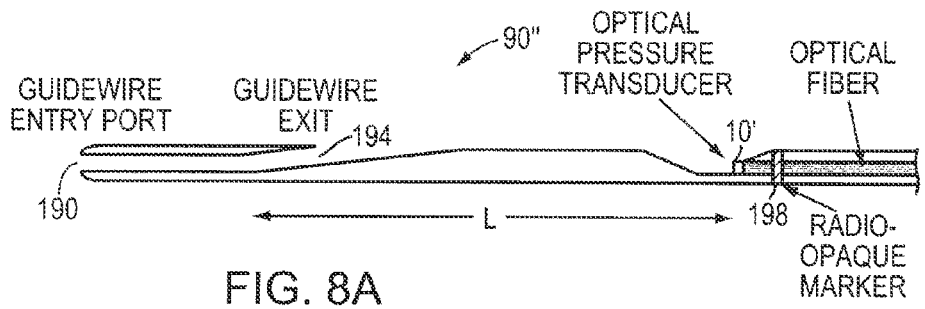
FIG. 8a is a cross-sectional view of the distal end of an embodiment of a rapid-exchange intravascular catheter with a single pressure sensing port constructed in accordance with the invention.
Figure 8B:
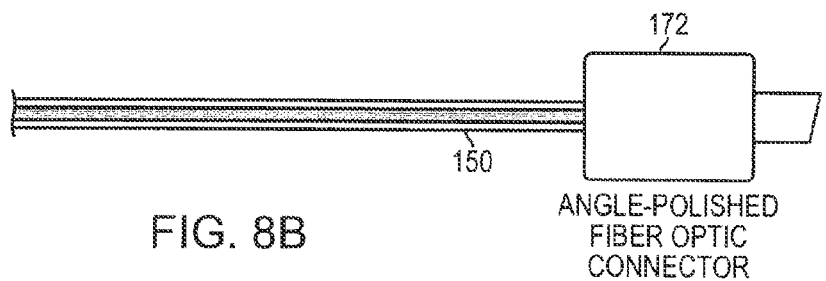

FIGS. 8(a-b) show yet another alternative construction of an optical pressure probe 90" that is suitable for intravascular pressure measurement with an FD-OCT system configured according to the various embodiments of the invention. Unlike the pressure probes 90, 90' illustrated in FIGS. 6 and 7, this version of the pressure probe is designed for rapid delivery over a primary guide wire.

In many instances, especially when an artery is tortuous or otherwise difficult to access, the clinician prefers to employ an independent primary guide wire rather than to steer the unsupported pressure probe to the target site. The guide wire (not shown) is inserted at the probe tip 190 and exits through the guide wire exit 194. The guide wire is inserted into the vessel and moved to the position of interest in the vessel. The pressure probe 90" is next inserted into the vessel over the guide wire and also moved to the place of interest in the vessel. The position of the pressure transducer can be monitored under x-ray imaging using the radio-opaque marker 198 located on the probe. The guide wire may then be removed and the pressure measurements performed.

Eliminating the need for steerability of the pressure probe 90" makes the rapid-exchange pressure wire easier and less costly to fabricate; however, to minimize restriction of blood flow, its cross section should be kept small. Therefore, to avoid inaccurate measurement of vascular resistance, the relatively large-diameter tip of the pressure probe must be placed far enough away from a tight vessel stenosis to prevent further restriction of blood flow. To satisfy this constraint, in one embodiment, the distance from the exit port of the guide wire to the pressure sensor (labeled 'L' in FIG. 8a) is set to 2-4 cm. The offset of the pressure sensor 10' relative to the tip 190 enables the user to place the largest-diameter segment of the probe outside of the stenosis during the measurement of pressure both distal and proximal to the stenosis.

The utility and ease of use of the rapid-exchange version of the pressure probe can be improved by modifying its construction according to FIGS. 9 (a-c). The distal end of the pressure probe 90" shown in this figure includes a series of ports 160' at evenly spaced intervals (typically 2-5 mm) that transmit the pressure at particular points along the axis of the artery to the inner lumen of the probe. An optical pressure transducer 10' at the tip of an optical fiber inside the lumen of the pressure probe senses the local pressure in the vicinity of the pressure ports. The optical fiber and attached pressure transducer are designed to translate longitudinally inside the lumen as the motor inside the probe interface pulls the fiber connector back at a constant speed. Before use, the probe is flushed with saline. A liquid seal at the proximal end between the optical fiber and the non-rotating shell over the body of the fiber-optic connector prevents the escape of fluid into the probe interface.

To perform a pressure measurement, the clinician, inserts the tip of probe 90''' across the target lesion and pushes it forward until the target lesion lies between the radio-opaque markers 198', 198'' on both sides of the series of pressure ports. The measurement is initiated by activating the automated pullback mechanism (part of the standard FD-OCT probe interface), which pulls the transducer 10' along the length of the probe 90''' lumen at a constant velocity adjacent the series of pressure-sensing ports 160'. The pressure measured as a function of time provides a profile of the pressure across the lesion.

Figure 9A:
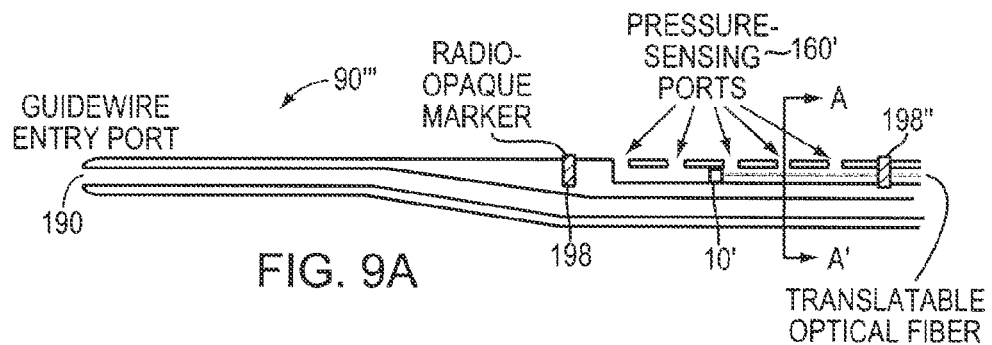
FIG. 9a is a cross-sectional view of the distal end of an embodiment of a rapid-exchange intravascular catheter with multiple pressure sensing ports.
Figure 9B:
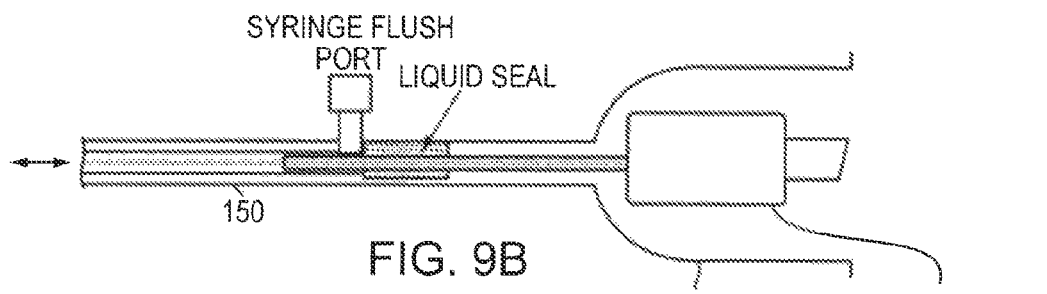
Figure 9C:
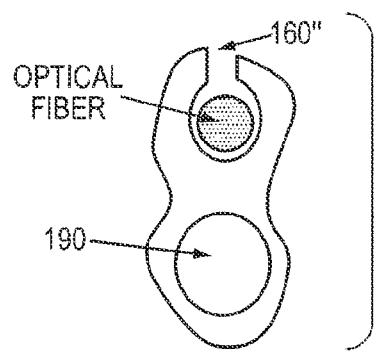
FIG. 9c is a section through A-A' of the embodiment of FIG. 9b.
Figure 9D:
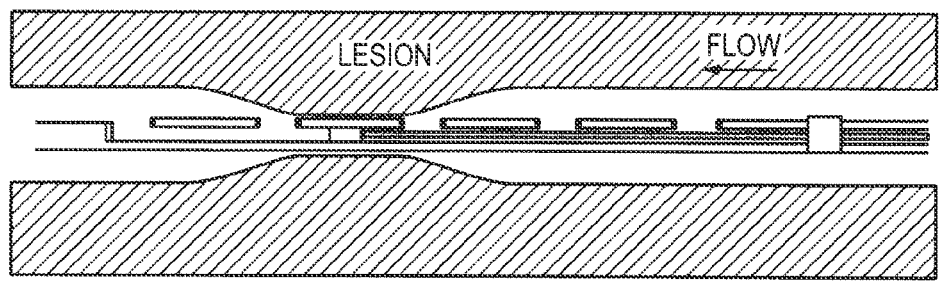
FIGS. 9d-f show a schematic diagram of an embodiment of a multi-hole probe and graphs of various pressure measurements made by the probe at various positions in a stenotic vessel.
Figure 9E:
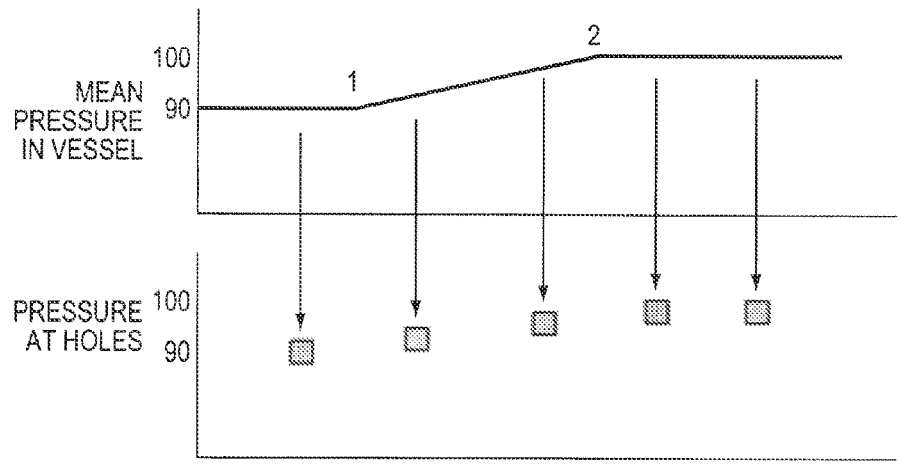
Figure 9F:
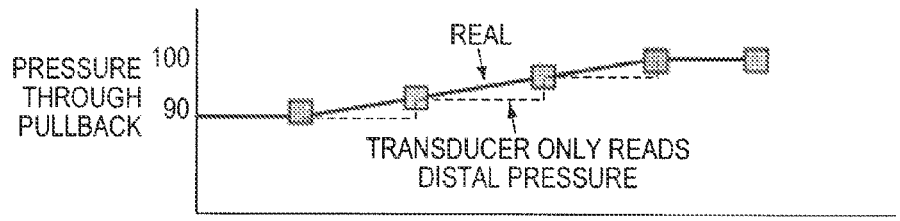

FIG. 9d shows an embodiment of a multi-hole probe within the lumen of a stenotic vessel. FIG. 9e shows the measured pressure at various positions in the vessel corresponding to the cross-section in FIG. 9d and the pressure values measured by the transducer at each of the holes in the probe. FIG. 9f shows the pressure readings by the transducer as it is moved by the individual holes. Because the transducer determines the pressure downstream (distal) from it, a stepped pressure measurement is obtained as the transducer moves by the individual holes. The pressure errors introduced by this technique are minimal.

Figure 10:
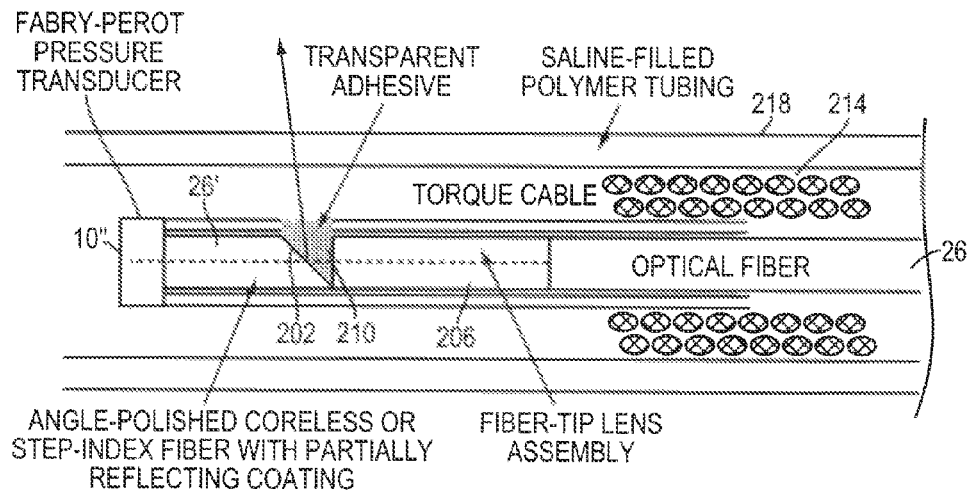
FIG. 10 is a cross-sectional view of the distal end of an embodiment of a rotational OCT imaging intravascular catheter that also functions as an intravascular pressure monitor.

FIG. 10 is a cross-sectional view of the tip of a catheter that combines the functions of an intravascular OCT imaging probe and a pressure wire. Depending on its construction, the combination catheter is compatible with the embodiments of the FD-OCT system shown in FIG. 2 and FIG. 5. The key feature of the combined catheter is the integration of the pressure transducer into the tip of the OCT imaging catheter. An optical Fabry-Perot pressure transducer 10'' is mounted on the distal end of a short length (typically 1-2 mm) of coreless or large-core step-index multimode fiber 26'. The distal end 202 of the fiber segment is polished at an angle of 40-50 degrees and coated with a thin dielectric or metallic film. To avoid excessive back-reflection from the distal end of a fiber-tip lens assembly 206, the fiber segment 26' with the attached transducer is glued to the fiber-tip lens assembly 206 with an adhesive 210 that matches the refractive index of the lens 206.

For use of the combination catheter with the FIG. 2 embodiment of the FD-OCT system in which both the OCT system and pressure transducer operate in the same wavelength band (typically 1260-1360 nm), the thin-film coating on the angle-polished end of the fiber segment is selected to reflect a large fraction (75-90%) of the incident light at specific wavelengths for OCT measurements and to transmit the remaining fraction to the transducer 10'' for pressure measurements. Since reflection from the Fabry-Perot cavity of the pressure transducer 10'' modulates the spectrum of the raw OCT interference signal a series of artifactual lines appear in the OCT image at a depth proportional to the modulation frequency. To avoid degradation of the OCT image caused by these lines, the zero point of the OCT interferometer can be set by setting the delay in the interferometer such that the lowest frequency of the displayed OCT signals exceeds the peak frequency of the spectral modulation.

For use of the combination catheter with the FIG. 5 embodiment of the FD-OCT system in which the OCT system and the pressure transducer operate in the first and second wavelength bands, respectively; the thin-film coating on the angle-polished end 202 of the fiber segment 26' is selected to reflect light maximally in the first wavelength band and to transmit light maximally in the second wavelength band. With the lens 206 and pressure transducer 10'' attached to its tip, the optical fiber mounts inside the lumen of torque wire 214 that rotates inside the catheter sheath 218. The catheter sheath is filled from the proximal port with saline or contrast medium. During pressure monitoring, the rotation of the torque wire 214 is turned off. The distal end of the catheter can employ either a monorail tip for rapid-exchange delivery, as in the embodiments shown in FIG. 8 and FIG. 9, or a spring tip for insertion in the artery without a guide wire, as shown in the pressure wire embodiments in FIG. 6 and FIG. 7.

Other beam-splitting arrangements at the catheter tip are also possible. For example, the fiber-tip lens assembly can be angle-polished and coated, rather than the fiber attached to the transducer. Also, a bulk optical component; such as miniature prism or mirror, can be employed as a beam splitter instead of an angle-polished optical fiber.

Figure 11:
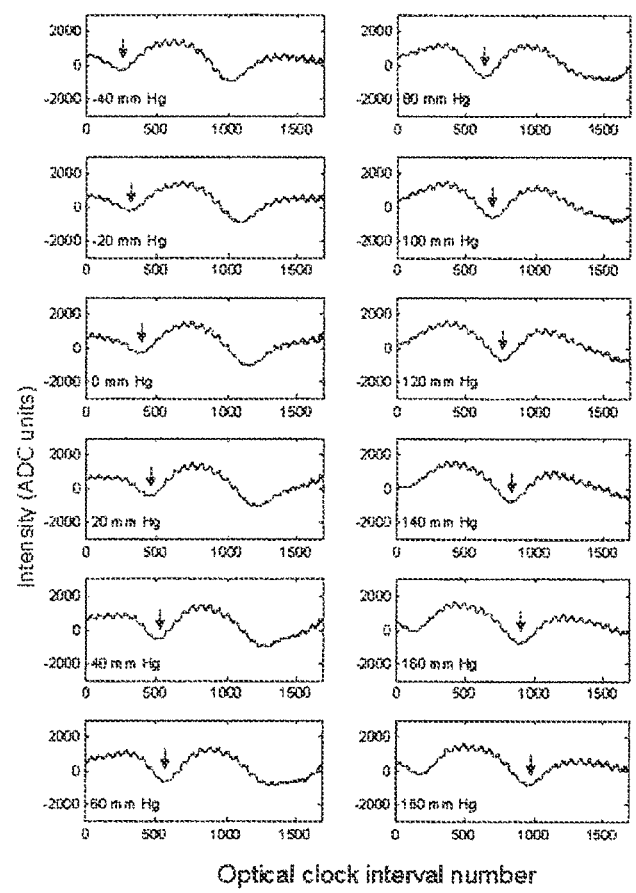
FIG. 11 shows examples of waveforms recorded from an optical pressure sensor by an optical coherence tomography system operating in the pressure-sensing mode.

FIG. 11 shows a set of common-mode interference signals acquired from an optical pressure probe connected to an FD-OCT system that was configured according to the embodiment of the invention shown in FIG. 2, operating in the pressure measurement mode. Acquired over a range of pressures (−40 mmHg<P<180 mmHg), the signals were recorded at successive optical dock intervals, in proportion to the wavenumber or optical frequency of the wavelength-swept laser. In this example, the abscissa spans an optical frequency range of 220-240 THz or, equivalently, a wavelength range of 1250-1360 nm. The low-frequency spectral modulation of the signal originates from reflections within the main Fabry-Perot cavity formed by the diaphragm and the body of the in the optical pressure transducer. The width of the cavity of the transducer in this example was approximately 17 μm. As shown by the arrows in FIG. 11, the low-frequency modulation pattern shifts to higher frequencies in proportion to pressure. The high-frequency spectral modulation superimposed on the signal was caused by reflection from a "parasitic cavity" in the transducer 10' formed by the interface between the input optical fiber 26' and the sensor body 22. Neither the frequency nor the amplitude of this parasitic modulation changes significantly with pressure.

The characteristics of the time-dependent interference signal generated by the pressure transducer at the output of the photoreceiver (see for example 120 in FIG. 4) of the FD-OCT system can be expressed as:

$$V(t) = KP_0(k)\lfloor r_{FP}(k,P) + r_p(k) \rfloor \quad (1)$$

where K is a constant, $P_0(k)$ is the optical power incident on the transducer; $r_{FP}(k, P)$ and $r_p(k)$ are, respectively, the reflectivities of the Fabry-Perot and parasitic cavities of the pressure transducer. The interference signal, power, and transducer reflectivities are functions of the optical wavenumber (k) of the light emitted by the laser, which varies as an arbitrary function of time (t). In the FD-OCT system, the signal voltage (V) from the photodetector 94 is sampled by the analog-to-digital converter 50 at evenly spaced wavenumber intervals, $k_n = k_0 + (n-1)\Delta k$; here, $k_0$ is the initial wavenumber of the laser sweep, $\Delta k$ is the wavenumber sample interval, and n=1, 2, . . . N, where N is the number of samples. According to these definitions, the recorded digital pressure signal can be expressed as an array of N values measured at successive optical clock intervals (in proportion to wavenumber), $$V_n = KP_0(k_n)[r_{FP}(k_n,P)+r_B(k_n)], \text{ for } n=0,1,2,\ldots N \quad (2)$$

The reflectivity $r_{FP}$ varies in relation to the pressure-dependent length, L(P), of the Fabry-Perot cavity, according to:

$$r_{FP}(k_n, P) = 1 - \frac{1}{1-|r_c|\sin[2k_nL(P)]} = \frac{|r_c|\sin[2k_nL(P)]}{|r_c|\sin[2k_nL(P)]-1} \quad (3)$$

Here, the magnitude of the effective reflection coefficient of the cavity, $|r_c|$, is approximately equal to the geometrical mean of the magnitudes of the reflection coefficients of the reflecting surfaces of the Fabry-Perot cavity. For most transducers, the length (L) decreases approximately linearly with pressure over a wide range of pressures. The parasitic reflectivity, $r_B(k)$, generated by M parasitic cavities within the transducer's body or packaging, generates pattern noise composed of sinusoids of different frequencies, $$r_p(k_n) = |r_{p1}|\sin(2k_nl_1) + |r_{p2}|\sin(2k_nl_2) + \ldots + |r_{pM}|\sin(2k_nl_M) \quad (4)$$

where $|r_{p1}|, |r_{p2}|, \ldots, |r_{pM}|$ are the magnitudes of the effective reflection coefficients of the parasitic cavities and $l_1$, $l_2, \ldots l_m$ are the lengths of the parasitic cavities.

These three equations, 2, 3 and 4 represent a mathematical model of the signal recorded by the FD-OCT system. The nominal Fabry-Perot cavity length (L) at a given pressure in Equation 3 is known from the manufacturing process. The reflection coefficient $|r_c|$ is determined by fitting signals measured from a sampled number of pressure transducers. In practice, a single parasitic cavity usually dominates, and its length and effective reflection coefficient can be determined by Fourier transformation of pressure signals measured from the sampled number of pressure transducers.

In accordance with the present invention, the algorithm for processing the pressure signal proceeds according to following steps:

First the signal is normalized by dividing the recorded signal array of voltages ($V_n$) by the laser power to obtain the normalized signal:

$$V_n^0 = V_n/P(k_n) \quad (5)$$

Next the parasitic cavity noise is removed by applying a Butterworth or equivalent low-pass filter to the normalized signal ($V_n^0$) with a cut-off frequency below that of the lowest frequency component of the reflection coefficients $r_p(k)$. The result is:

$$V_{n,F}^0 = LPF\{V_n^0\} \quad (6)$$

where LPF{ } represents the low-pass filtering operation. Next the spectral null, the sample wavenumber at which the amplitude of $V_{n,F}^0$ is lowest, is detected. $V_{n,F}^0$ is first convolved with a template array of values proportional to $r_{FP}(k)$, with $|r_c|$ and L(P) determined by fitting filtered arrays measured from a sample of transducers at reference pressures. The spectral null of $V_{n,F}^0$ occurs at the array index $n_{min}$ at which the amplitude of the convolved is maximum. Alternatively, the minimum, maximum or steepest edge of $V_{n,F}^0$ can be located by conventional differentiation or gradient-search methods known to persons skilled in the art.

The spectral null is then tracked and unwrapped. If more than one spectral null of $V_{n,F}^0$ occurs within the pressure range of interest or nulls move out of the laser's wavelength band at the extremes of the pressure range, the position of nulls can be tracked across multiple laser sweeps to extend the pressure measurement range. Tracking can be accomplished by standard phase unwrapping techniques applied to a sequence of stored $V_{n,F}^0$ array values.

Figure 12:
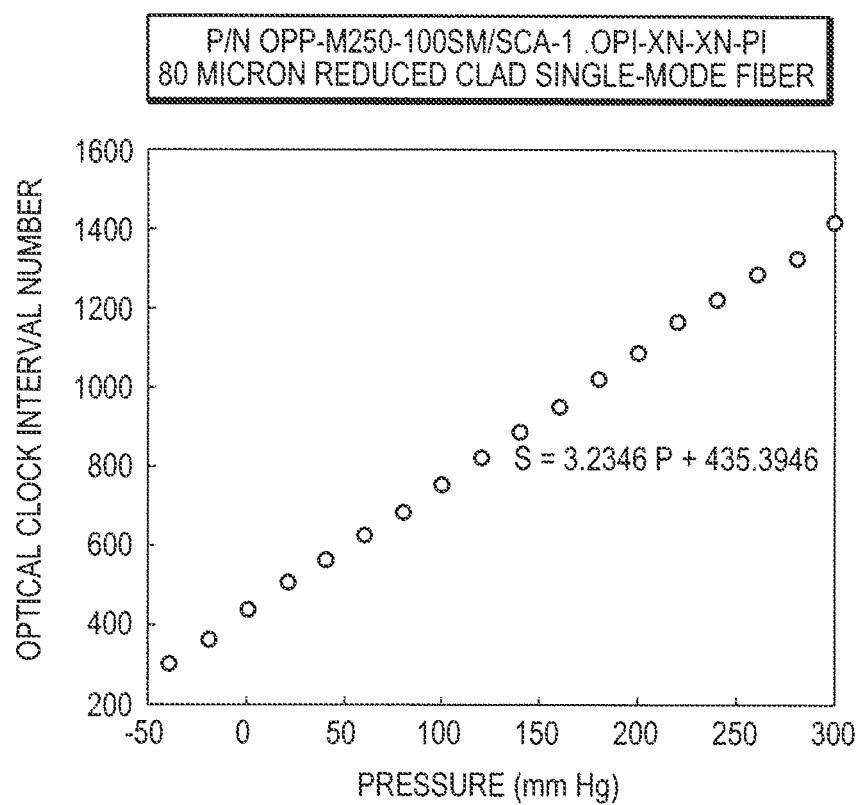
FIG. 12 is an example of a calibration curve of an optical pressure sensor.

FIG. 12 shows a calibration curve of a typical pressure transducer. The curve was obtained by applying the above algorithm to the raw pressure signals in FIG. 11. Since the optical clock interval number at which the spectral null occurs, $n_{min}$, varies approximately in linear proportion to the applied pressure, the pressure can be estimated accurately from $n_{min}$ once the slope and offset of the calibration curve are known. In practice, a polynomial function is used to fit the calibration curve of an individual pressure probe or catheter and the stored coefficients are employed to estimate pressure from measured $n_{min}$ values.

Figure 13:
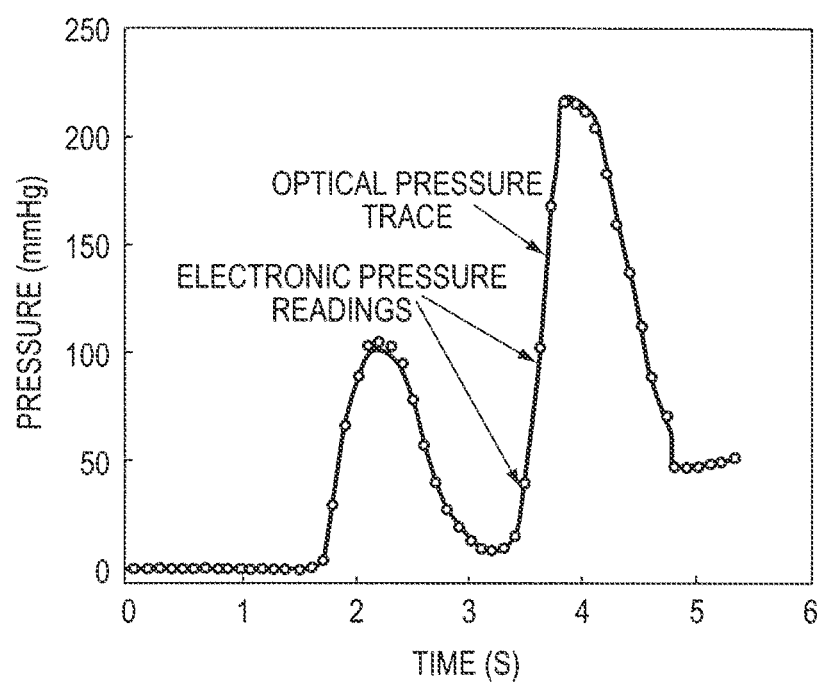
FIG. 13 compares dynamic pressure reading obtained from an electronic pressure sensor and an optical pressure sensor configured to operate with an FD-OCT system in accordance with the present invention.
Figure 14B:
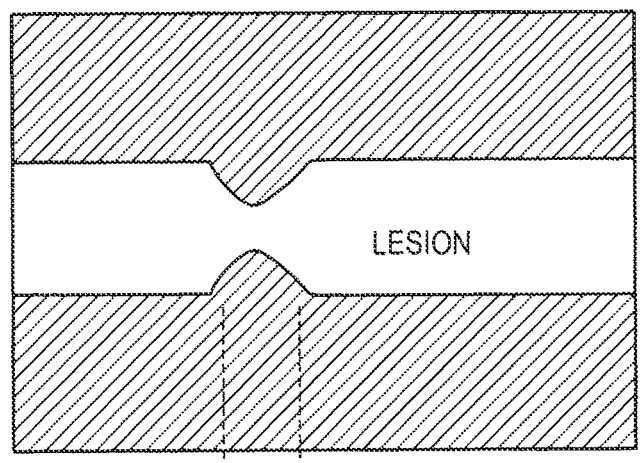
FIGS. 14 (a, b) show an example of dynamic pressure readings obtained from an optical pressure sensor during pullback through a model of a stenosed blood vessel and the corresponding region in the vessel at which the readings were taken.
Figure 14A:
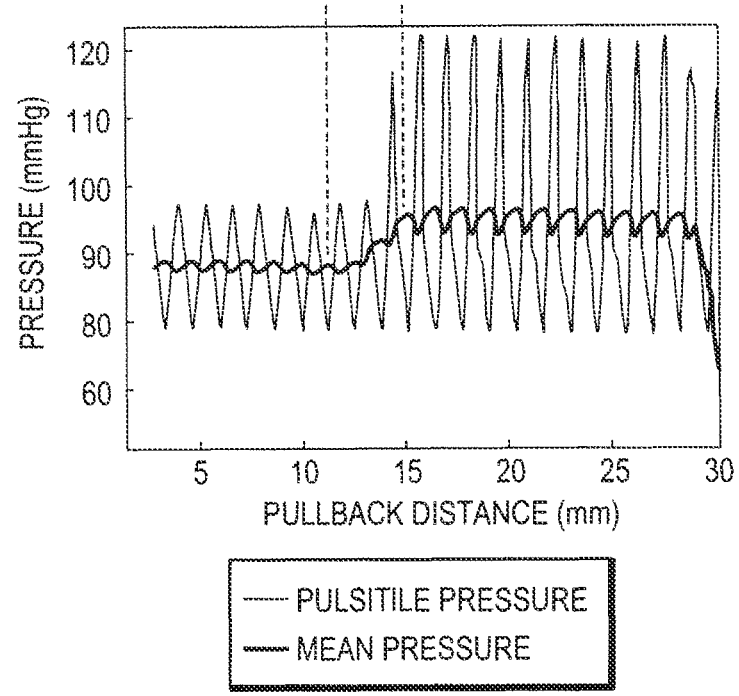

FIG. 13 shows dynamic pressure waveforms measured by the same pressure probe from which the raw signals in FIG. 11 were obtained. In this example, good correspondence compared to a commercial strain-gage transducer was obtained by using a simple first-order polynomial (linear) calibration curve. FIGS. 14A, B show the pressure waveforms measured by the pressure probe across a tight stenosis in a simulated artery. In this experiment, the pressure-sensing segment of the pressure probe was pulled through the stenosis at a constant speed by a motor in the probe interface. The sharp reductions in both mean and pulsatile pressures provide clear evidence of the flow resistance imposed by the stenosis.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Variations, modification, and other implementations of what is described herein will occur to those of ordinary skill in the art without departing from the spirit and scope of the invention as claimed. Accordingly, the invention is to be defined not by the preceding illustrative description, but instead by the spirit and scope of the following claims.

What is claimed is:

1. A method of determining pressure in a vessel as measured by an optical pressure transducer in an OCT system comprising an interferometer having a photoreceiver located in a detector arm of the interferometer and having an optical pressure transducer defining a cavity located within an OCT probe in a sample arm of the interferometer, comprising the steps of:
    sampling a signal from the photoreceiver to form a sampled pressure signal;
    normalizing the sampled signal to obtain a normalized sampled pressure signal;
    removing cavity noise to form a cleaned normalized sampled pressure signal;
    finding a minimum value in the cleaned normalized sampled pressure signal;
    tracking the minimum value of the cleaned normalized sampled pressure signal; and
    comparing the minimum value of the cleaned normalized sampled pressure signal to a calibration curve to determine a pressure within the vessel.

2. The method of claim 1 wherein the minimum value is determined by one of convolution, differentiation and gradient searching.

3. The method of claim 1 further comprising the steps of:
inserting a catheter having the optical pressure transducer into the vessel; and
moving the optical pressure transducer within the catheter.

4. The method of claim 1 further comprising transmitting light from a light source through the vessel to the optical pressure transducer.

5. The method of claim 1 further comprising rotating the OCT probe to acquire an OCT image and terminating the rotation of the OCT probe during the pressure measurement.

6. A method of determining pressure in a blood vessel comprising
transmitting light towards an optical pressure transducer from a light source, the light source in optical communication with an interferometer comprising a first arm and a second arm;
detecting light reflected from the optical pressure transducer using a photoreceiver in optical communication with the first arm, the optical pressure transducer defining a cavity;
sampling a signal from the photoreceiver to form a sampled pressure signal;
normalizing the sampled signal to obtain a normalized sampled pressure signal;
removing parasitic cavity noise generated by a parasitic cavity of the optical pressure transducer to form a cleaned normalized sampled pressure signal;
finding a minimum value in the cleaned normalized sampled pressure signal;
tracking the minimum value of the cleaned normalized sampled pressure signal; and
comparing the minimum value of the cleaned normalized sampled pressure signal to a calibration curve to determine a pressure in the blood vessel.

7. A method of determining pressure in a vessel using an optical pressure transducer having a cavity, the method comprising the steps of:
providing a measuring beam in a measuring arm of an OCT interferometer, the interferometer having a photoreceiver;
permitting a portion of the measuring beam to interrogate the cavity of the optical pressure transducer;
sampling a pressure signal generated by the photoreceiver in response to the measuring beam being reflected by the optical pressure transducer;
normalizing the sampled pressure signal to obtain a normalized sampled pressure signal;
removing parasitic noise generated by a parasitic cavity of the optical pressure transducer to form a cleaned normalized sampled pressure signal;
determining a spectral null in the cleaned normalized sampled pressure signal;
tracking the spectral null;
unwrapping the tracked spectral null; and
comparing a location of the spectral null to a spectral null calibration curve to determine a pressure in the vessel.

8. The method of claim 7 wherein the step of removing parasitic noise comprises passing the normalized sampled pressure signal through a low pass filter.

9. The method of claim 8 wherein the low pass filter has a cut-off frequency less than the lowest frequency component of the reflection coefficients of the parasitic cavity of the optical pressure transducer.

10. The method of claim 7 wherein the and unwrapping is performed by phase unwrapping.

11. A method of determining pressure in a vessel using an OCT probe having an optical pressure transducer having a cavity, the method comprising the steps of:
providing a measuring beam in a measuring arm of an OCT interferometer, the interferometer having a photoreceiver;
transmitting a portion of the measuring beam so as to pass through and reflect from the cavity of the optical pressure transducer;
receiving a pressure signal generated by the photoreceiver in the interferometer in response to the cavity reflected measuring beam;
sampling the pressure signal generated by the photoreceiver in response to the measuring beam being reflected by the optical pressure transducer;
normalizing the sampled pressure signal to obtain a normalized sampled pressure signal;
removing parasitic cavity noise, generated by a parasitic cavity, from the normalized sampled pressure signal to provide a cleaned pressure signal;
determining a spectral null in the cleaned pressure signal;
tracking the spectral null; and
comparing the location of the spectral null to a spectral null calibration curve to determine a pressure in the vessel.

12. The method of claim 11 wherein the location of the spectral null is measured in optical clock intervals.

13. The method of claim 12 wherein the parasitic cavity comprises a parasitic reflection coefficient and wherein the step of removing the parasitic noise comprises using a low pass filter.

14. The method of claim 13 where the step of filtering removes frequencies greater than the lowest frequency component of the parasitic reflection coefficient.

15. The method of claim 14 wherein the parasitic reflection coefficient is determined by Fourier transform.

16. A method of determining pressure in a vessel using an OCT probe having an optical pressure transducer having a cavity, and an interferometer having a photoreceiver and a measuring beam, the method the steps of:
transmitting a portion of the measuring beam of the OCT probe so as to pass through and reflect from the cavity of the optical pressure transducer;
receiving, by the photoreceiver, a portion of the reflected measuring beam;
sampling a pressure signal generated by the photoreceiver in response to the measuring beam being reflected by the optical pressure transducer;
normalizing the sampled pressure signal to obtain a normalized sampled pressure signal;
removing parasitic cavity noise from the normalized sampled pressure signal to form a cleaned normalized sampled pressure signal;
determining a spectral null in the cleaned normalized sampled pressure signal; and
comparing a location of the spectral null to a spectral null calibration curve to determine a pressure in the vessel.

17. The method of claim 16 further comprising the step of tracking the spectral null.

* * * * *